United States Patent [19]

Freenor, III

[11] 4,140,514
[45] Feb. 20, 1979

[54] CYCLIC DITHIOPHOSPITES

[75] Inventor: Francis J. Freenor, III, Richmond, Calif.

[73] Assignee: Chevron Research Company, San Francisco, Calif.

[21] Appl. No.: 882,702

[22] Filed: Mar. 2, 1978

Related U.S. Application Data

[63] Continuation-in-part of Ser. No. 825,008, Aug. 16, 1977, abandoned, which is a continuation-in-part of Ser. No. 616,343, Sep. 24, 1975, abandoned.

[51] Int. Cl.² .............................................. A01N 9/36
[52] U.S. Cl. ...................................... 71/87; 424/209; 260/937
[58] Field of Search ............................ 424/209; 71/87; 260/937

[56] References Cited

U.S. PATENT DOCUMENTS

| 2,892,862 | 6/1959 | Lanham | 260/937 |
|---|---|---|---|
| 2,927,122 | 3/1960 | Schrader | 260/937 X |
| 3,116,201 | 12/1963 | Whetstone et al. | 260/937 X |
| 3,159,664 | 12/1964 | Bartlett | 424/209 X |
| 3,463,836 | 8/1969 | Aichenegg | 71/87 X |
| 3,562,390 | 2/1971 | Hamm | 424/209 |
| 3,760,042 | 9/1973 | Bertger et al. | 71/87 X |
| 3,812,219 | 5/1974 | Clovis et al. | 260/936 |

OTHER PUBLICATIONS

Arbuzov, et al; C. A., 47 (1953), 4833d.

Primary Examiner—Joseph Paul Brust
Attorney, Agent, or Firm—Dix A. Newell; T. G. DeJonghe

[57] ABSTRACT

Compounds of the formula

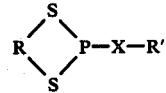

wherein R is an alkylene diradical of 2 to 3 carbon atoms, X is oxygen or sulfur, and R' is a hydrocarbyl group possessing herbicidal activity.

5 Claims, No Drawings

CYCLIC DITHIOPHOSPITES

RELATED APPLICATIONS

This application is a continuation-in-part of application Ser. No. 825,008, filed Aug. 16, 1977, which in turn, is a continuation-in-part of application Ser. No. 616,343, filed Sept. 24, 1975, both now abandoned. The disclosure of Ser. No. 616,343 is incorporated herein by reference.

BACKGROUND OF THE INVENTION

1. Field

The present invention is directed to cyclic dithiophosphites and their use as insecticides, herbicides and/or fungicides.

2. Prior Art

Chem Abstr. 1953: 4833d (Izvest. Akad. Nauk. SSSR Ot dal, Kina, Nauk, 1952, 453-8) discloses methyl- and ethyl-S,S-ethylene phosphorodithioite as hypergolic fuel.

U.S. Pat. Nos. 2,892,862 and 3,812,219 disclose heterocyclic phosphite esters useful as intermediates in the production of other compounds. See also Journal of the American Chemical Society 72, 5491-7 (1970). No.

U.S. Pat. 3,463,836 discloses S,S-hydrocarbyl-S-trichloroethyl or dichlorovinyl phosphates as herbicides, fungicides and insecticides.

U.S. Pat. No. 3,277,211 discloses alkyl alkylene phosphites useful as intermediates in the production of other compounds.

German Pat. No. 2,100,388 discloses certain organophosphorus compounds as defoliants.

DESCRIPTION OF THE INVENTION

The novel compounds of the present invention can be represented by the general formula (I)

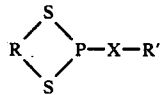
(I)

wherein R is an alkylene diradical of 2 to 3 carbon atoms, X is oxygen or sulfur, and R' is a hydrocarbyl group of 1 to 12 carbon atoms substituted with 0 to 5 halogen atoms of atomic number 9 to 35 (fluorine, chlorine or bromine), 0 to 2 nitro groups, 0 to 2 alkoxy groups of 1 to 4 carbon atoms, 0 to 2 alkylthio groups of 1 to 4 carbon atoms, or 0 to 1 carbalkoxy group of 2 to 6 carbon atoms. Preferably only one type of substituent is associated with the R' hydrocarbyl group. The compounds methyl- and ethyl-S,S-ethylene phosphorodithioite per se are not claimed as compounds of this invention, although the use of the compounds as pesticides is claimed.

In other words, the novel compounds of the present invention are defined by the above formula wherein: (a) R is dimethylene, X is O, R' is vinyl, ethynyl, hydrocarbyl of 3 to 12 carbon atoms, hydrocarbyl of 1 to 12 carbon atoms substitutued with 1 to 5 halogen atoms of atomic number 9 to 35 (fluorine, chlorine or bromine), 1 to 2 nitro groups, 1 to 2 alkoxy groups of 1 to 4 carbon atoms, 1 to 2 alkylthio groups of 1 to 4 carbon atoms or a carbalkoxy group of 2 to 6 carbon atoms; (b) R is dimethylene, X is S, R' is hydrocarbyl of 1 to 12 carbon atoms substituted with from 0 to 5 halogen atoms of atomic number 9 to 35, 0 to 2 nitro groups, 0 to 2 alkoxy groups of 1 to 4 carbon atoms, 0 to 2 alkylthio groups of 1 to 4 carbon atoms, or 0 to 1 carbalkoxy group of 2 to 6 carbon atoms; (c) R is 1,2-propylene or trimethylene, x is O or S, and R' is hydrocarbyl of 1 to 12 carbon atoms substituted with from 0 to 5 halogen atoms of atomic number 9 to 35, 0 to 2 nitro groups, 0 to 2 alkoxy groups of 1 to 4 carbon atoms, 0 to 2 alkylthio groups of 1 to 4 carbon atoms, or 0 to 1 carbalkoxy group of 2 to 6 carbon atoms.

Preferably R is dimethylene or 1,2-propylene, X is oxygen or sulfur, and R' is a hydrocarbyl group of 1 to 10 carbon atoms substituted with 0 to 2 halogen atoms, 0 to 1 nitro group, 0 to 1 alkoxy group of 1 to 4 carbon atoms, 0 to 1 alkylthio group of 1 to 4 carbon atoms or 0 to 1 carbalkoxy group of 2 to 6 carbon atoms. Again, the compounds wherein R is dimethylene, X is oxygen, and R' is methyl or ethyl are not claimed per se as a part of this invention, although the pesticidal use of such compounds is claimed.

Preferably when R is dimethylene and X is oxygen, R' is alkyl of 3 to 5 carbon atoms, preferably 3 to 4 carbon atoms, alkyl of 1 to 5 carbon atoms (preferably 1 to 4) substituted with a nitro group, or cycloalkyl of 5 to 6 carbon atoms, preferably a cyclopentyl group. When R is dimethylene and x is sulfur, R' is preferably carboethoxymethyl or 2-methylpropyl.

Preferred insecticides are the compounds wherein R is dimethylene or 1,2-propylene, X is oxygen and R' is a straight-chain alkyl of 1 to 5 carbon atoms, cycloalkyl of 5 to 6 carbon atoms or alkoxyalkyl of 2 to 4 carbon atoms, preferably methoxyethyl or ethoxyethyl.

According to a preferred embodiment of the present invention, a method is provided for controlling, that is, inhibiting and/or killing, the growth of undesirable vegetation, which method comprises applying to the undesirable vegetation or to the growth medium of the undesirable vegetation an herbicidally effective amount of a compound of the formula

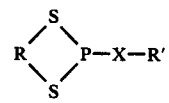

wherein:
(a) when R is dimethylene, X is oxygen and R' is phenyl; phenyl substituted with 1 to 5 halogen atoms, preferably fluorine or chlorine, more preferably 2 to 5 halogens or 1 fluorine atom; phenyl substituted with one alkyl group of 1 to 2 carbon atoms; phenyl substituted with one nitro group; benzyl; benzyl substituted with a chlorine or methyl group. Particularly preferred R' groups when X is oxygen are phenyl or phenyl substituted with 2 to 5 halogens, other than 2,4-dichlorophenyl. Also, I have found that phenyl substituted with one fluorine atom is a particularly advantageous R' group for the compound when using the compound as an herbicide.

Alternatively, (b) when R is dimethylene but X is sulfur instead of oxygen, R' can be phenyl; cycloalkyl of 5 to 6 carbon atoms or normal (straight-chain) alkyl of 5 to 10 carbon atoms.

Lastly, (c), when R is 1,2-propylene or trimethylene and X is oxygen or sulfur, R' can be normal alkyl of 1 to 10 carbon atoms or normal alkyl of 1 to 10 carbon atoms substituted with 1 to 3 halogen atoms; phenyl; phenyl substituted with 1 to 5 halogen agoms; preferably 1 to 2 chlorine or fluorine atoms, more preferably chlorine, an alkyl group of 1 to 4 carbon atoms, or a nitro group; benzyl; benzyl substituted with 1 to 5 halogen atoms, preferably 1 to 2 fluorine and chlorine atoms, most preferably chlorine, an alkyl group of 1 to 4 carbon atoms or a nitro group; or alkylene radical of 1 to 3 carbon atoms substituted with a carbalkoxy group of 2 to 6 carbon atoms.

When R is 1,2-propylene or trimethylene and X is oxygen or sulfur, particularly preferred normal alkyl groups for R' contain 1 or 3 to 10 carbon atoms either unsubstituted or substituted with 1 to 3 halogen atoms such as chlorine or fluorine atoms. Also, when R is 1,2-propylene or trimethylene and X is oxygen or sulfur, R' is preferably the last-mentioned n-alkyl group; phenyl; phenyl with a chlorine or fluorine or nitro atom or an alkyl group of 1 to 10 carbon atoms or a chloromethyl group.

Particularly preferred compounds for herbicidal use, especially for post-emergent broadleaf herbicidal use, are alkyl phenol derivatives, that is, compounds of the formula

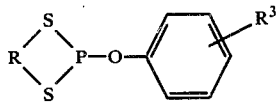

where R is ethylene or 1,2-propylene and $R^3$ is a $C_1$ to $C_4$ alkyl. In this regard, reference can be made to examples 43 and 57 hereinbelow.

Another preferred group of compounds in this regard are those benzyl derivatives, that is, compounds of the formula

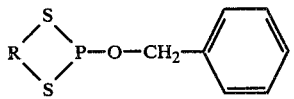

where R is ethylene or 1,2-propylene. In this regard, reference can be made to examples 32 and 53.

I have found that a particularly preferred trithioite for use as an herbicide, especially as a post-emergent herbicide, is carbethoxy methyl-1,3-propylene phosphorotrithioite. In this regard, reference can be made to example 126.

In the examples, Table IIa shows many structurally close compounds in the first approximately one-half of the table which are excluded from the present invention.

According to another embodiment of the present invention, an herbicidal composition is provided comprising a compound as set forth in the above embodiments, and an inert carrier.

Representative alkyl groups (substituted and unsubstituted) which R' may represent are ethyl, propyl, n-butyl, n-pentyl, n-heptyl, n-nonyl, n-dodecyl, 1,2-dichloroethyl, 2,2-dibromomethyl, 1-chloro-2-bromoethyl, 2-methoxyethyl, 3-methoxypropyl, ethyltiomethyl, 6-methoxyhexyl, 7-ethoxyheptyl, 3-octyloxypropyl, 2-butoxyethyl, propoxymethyl, propylthiomethyl, 2-nitroethyl, 2-nitropropyl, 2,4-dimethylhexyl, 3,5-dimethyloctyl, 3-ethylpentyl, carbomethoxyethyl, carbethoxyethyl, etc.

Representative alkenyl groups (substituted and unsubstituted) which R' may represent are allyl, crotyl, propenyl, 4-hexenyl, 11-dodecenyl, 8-decenyl, 3-chloroallyl, 1-chloroallyl, 3,3-dichloroallyl, 3-bromophenyl, 4-chlorocrotyl, 4-methoxycrotyl, etc.

Representative cycloalkyl groups (substituted and unsubstituted) which R' may represent are cyclopentyl, cyclohexyl, cyclooctyl, cyclododecyl, 2chlorocyclohexyl, 4-methoxycyclohexyl, 2,4-dichlorocyclopentyl, 2-bromocycloheptyl, etc.

Representative aryl groups (substituted and unsubstituted) which R' may represent are phenyl, benzyl, 2-methylphenyl, 3-methylphenyl, 4-methylphenyl, 2-isopropylphenyl, 3-t-butylphenyl, 4-ethylphenyl, 2-methylbenzyl, 2-phenylpropyl, 4-phenylbutyl, 2-phenylpentyl, 2,4-dimethylphenyl, 3,5-dimethylphenyl, 2-chlorophenyl, 3-bromobenzyl, 4-bromphenyl, 2-chlorobenzyl, 2,4-dichlorophenyl, 3,5-dichlorobenzyl, 2-bromo-4-chlorophenyl, 2-methyl-4-methoxyphenyl, 2,4-dimethoxybenzyl, 2-phenyl-3-chloropropyl, 2-methoxyphenyl, 4-ethoxybenzyl, 4-isopropoxyphenyl, 2-methyl-4-methoxyphenyl, 2,4-dimethoxybenzyl, isopropoxyphenyl, 2-methyl-4-methoxyphenyl, 2,4-dimethoxybenzyl, 3-butoxyphenyl, 2-chloro-4-methoxyphenyl, 2-ethoxy-4-bromobenzyl, 2-(4'-methoxyphenyl)ethyl, 2-nitrobenzyl, 3-ethyl-5-nitrophenyl, 2-fluorophenyl, 3-fluorobenzyl, 2,4-difluorophenyl, 3-trifluoromethylphenyl, 3-fluorobenzyl, 2,4-difluorophenyl, 2-fluoro-4-methylphenyl, 2-fluoro-4-t-butylbenzyl, etc.

The following compounds are illustrative of the compounds of the present invention contemplated by formula (I):

n-hexyl-S,S-ethylene phosphorodithioite,
3-chloroallyl-S,S-ethylene phosphorodithioite,
n-nonyl-S,S-1,2-propylene phosphorodithioite,
4-methoxyphenyl-S,S-ethylene phosphorodithioite,
carbethoxymethyl-S,S-trimethylene phosphorodithioite,
cyclopentyl ethylene phosphorotrithioite,
n-heptyl trimethylene phosphorotrithioite,
crotyl 1,2-propylene phosphorotrithioite,
carbomethoxymethyl trimethylene phosphorotrithioite,
carbethoxymethyl ethylene phosphorotrithioite,
carbethoxymethyl-1,2-propylene phosphorotrithioite, etc.

The compounds of this invention are prepared by the reaction of an alcohol, phenol, mercaptan or thiphenol with an appropriate cyclic dithiophosphoryl chloride, as follows:

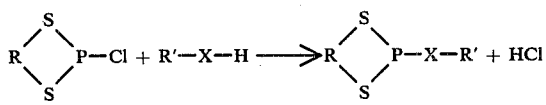

wherein X, R and R' are as defined previously.

This reaction is carried out under anhydrous conditions and in an atmosphere of nitrogen. Generally, a solvent is employed to facilitate the reaction, although excess alcohol or mercaptan may be employed instead of a separate solvent. Satisfactory solvents include inert organic liquids such as diethylether, tetrahydrofuran, dioxane, dimethoxyethane, etc. The quantity of solvent must be sufficient to dissolve the two reactants and usually ranges from 5 to 50 times the total volume of the reactants.

A base is included in the reaction mixture to scavenge the by-product hydrogen chloride. At least a molar amount of base based on the cyclic phosphoryl chloride is used, preferably a small excess of about 10% is desired. Bases suitable for this use include triethylamine, pyridine, triethylene diamine, etc.

In order to ensure anhydrous reaction conditions, molecular sieves are frequently included in the reaction system. However, this is an optional refinement in carrying out the reaction.

The preferred process involves dissolving the alcohol or mercaptan and the base in the solvent and then slowly adding the cyclic phosphoryl chloride while maintaining the reaction temperature in the range of 20° C. to 50° C., preferably 25–35° C. The rate of addition must be controlled so that the temperature remains within this range.

At the completion of the reaction, the insoluble precipitate is removed by filtration. The solvent is removed from the filtrate by distillation, evaporation, or similar means. In general, the crude product is satisfactory for pesticidal use. However, it may be purified by the usual techniques of distillation, crystallization, and the like.

The alcohols, mercaptans, phenols, and thiophenols employed in the above reaction are well-known compounds, usually commercially available or readily prepared by the usual methods found in the chemical literature.

The cyclic alkyldithiophosphoryl chlorides are prepared by the reaction of phosphorus trichloride with a 1,2- or a 1,3-dimercaptan, thus:

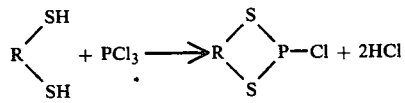

wherein R is as previously defined.

The above reaction of ethane dimercaptan with PCL$_3$ is described in Izvest. Akad. Nauk. SSSR Ot dal. Kina. Nauk. 1952, 453–8 (Chem. Abst. 1953: 4833d). The reactions of 1,3- and 1,2-propane dimercaptan are carried out in a similar manner to give the corresponding cyclic dithiophosphites.

EXAMPLES

The following examples illustrate preparation of representative compounds of this class.

EXAMPLE 1 — n-Butyl Ethylene Phosphorotrithioite

A 250-ml round-bottom flask was swept out with nitrogen and charged with 100 ml of diethylether, 3.82 g (0.0423 mol) of n-butyl mercaptan, and 4.8 g (0.0475 mol) of triethylamine. Nitrogen was bubbled through this solution and then 6.72 g (0.0423 mol) of ethylene dithiophosphoryl chloride was added dropwise. The reaction temperature was held at 25–30° C. After all the phosphoryl chloride was added, the reaction mixture was filtered, and the resulting filtrate was evaporated to dryness on a rotovac apparatus. In this way there was obtained 7.9 g of a liquid product. Analysis, calculated for C$_6$H$_{13}$S$_3$P: %S, calc. 45.2, found 42.5; %P, calc, 14.6, found 13.9. An infrared spectrum showed sharp adsorption peaks at 6.8, 7.05, 7.8, 8.15, 10.6 and 12.0 microns.

EXAMPLE 2 — Crotyl S,S-Ethylene Phosphorodithioite

A 250-ml round-bottom flask was swept out with nitrogen and charged with 100 ml of diethyl ether, 3.34 g (0.0463 mol) of crotyl alcohol, 5.5 g (0.0509 mol) of triethylamine, and several 3-Angstrom molecular sieves. Then 7.35 g (0.0463 mol) of ethylene dithiophosphoryl chloride was added dropwise while maintaining the reaction temperature at about 30° C. After all phosphoryl chloride was added, the reaction mixture was allowed to stand for 16 hours. The product was filtered and then the filtrate was evaporated on a rotovac apparatus. In this way there was obtained 8.48 g of a liquid product. Analysis, calculated for C$_6$H$_{11}$S$_2$OP: %S, calc. 33.0, found 31.5; %P, calc. 15.0, found 15.8. An infrared spectrum showed strong adsorption peaks at 6.9, 7.05, 7.8, 8.1, 9.3, 9.8, 10.2–10.5, 12.0, 12.5–12.6 and 13.7 microns.

EXAMPLE 3 — 1,1,1-Trichloro-2-Propyl-S,S-Ethylene Phosphorodithioite

This reaction was carried out essentially the same as Example 2, utilizing 5.16 g (0.0346 mol) of triethylamine and 5.01 g (0.0315 mol) of ethylene dithiophosphoryl chloride in 100 ml of ether. The product was a liquid weighing 9.03 g. Analysis, calculated for C$_5$H$_8$OS$_2$Cl$_3$P: %Cl, calc. 37.1, found 37.6; %S, calc. 22.4, found 22.1; %P, calc. 10.8, found 10.5. An infrared spectrum showed strong adsorption peaks at 6.9, 7.1, 7.3, 7.5, 7.85, 8.9, 9.1, 9.45, 10.35, 11.0–11.2, 12.1–12.2, 12.7–12.8, and 13.7–14.0 microns.

EXAMPLE 4 — Phenyl Ethylene Phosphorotrithioite

This reaction was carried out essentially the same as Example 2, utilizing 4.27 g (0.0388 mol) of thiophenol, 4.31 g (0.0426 mol) of triethylamine, and 6.15 g (0.0388 mol) of ethylene dithiophosphoryl chloride in 100 ml of ether. The liquid product weighed 8.81 g. Analysis, calculated for C$_8$H$_9$S$_3$P: %S, calc. 41.3, found 38.7; %P, calc. 13.3, found 12.4. An infrared spectrum had strong adsorption peaks at 6.3, 6.8, 6.95, 7.1, 7.8, 9.75, 10.65, 12.0, 13.4, and 14.45 microns.

EXAMPLE 5 — 2-Fluorophenyl-S,S-Trimethylene Phosphorodithioite

This example was carried out essentially the same as Example 5, utilizing 3.61 g (0.322 mol) of 2-fluorophenol, 3.58 g (0.0354 mol) of triethylamine and 5.56 g (0.0322 mol) of trimethylene dithiophosphoryl chloride to give 7.72 g of a liquid product. Analysis, calculated for C$_9$H$_{10}$OS$_2$FP: %S, calc. 25.8, found 26.5; %P, calc., 12.5, found 14.2. An infrared spectrum had strong adsorption peaks at 6.2, 6.6, 6.8, 6.9–7.0, 7.9, 8.3–8.4, 9.0, 9.6, 9.9, 10.6, 11.0, 11.2–11.4, 12.5–12.7, and 13.0–13.4 microns.

EXAMPLE 6 — Isobutyl-1,2-Propylene Phosphorotrithioite

This compound was prepared by the procedure of Example 1, utilizing 3.13 g (0.0347 mol) of isobutyl mercaptan, 3.85 g (0.381 mol) of triethylamine, and 5.98 g (0.0347 mol) of 1,2-propylene dithiophosphoryl chloride to give 7.55 g of liquid product. Analysis, calculated for C$_7$H$_{15}$S$_3$P: %S, calc., 42.5, found 38.5; %P, calc., 13.7, found 13.5. The infrared spectrum had sharp adsorption peaks at 6.9, 6.95, 7.1, 7.3, 7.6, 8.1, 9.9 and 10.5 microns.

Other compounds were prepared by variations of the above procedures. These compounds are listed in Table I.

UTILITY

Certain of the compounds of the present invention are herbicidal in pre- and/or post-emergent applications. For pre-emergent control of undesirable vegetation, these compounds will be applied in herbicidal quantities to the environment, e.g., soil infested with seeds and/or seedlings of such vegetation. Such application will inhibit the growth of or kill the seeds, germinating seeds and seedlings. For post-emergent applications, the compounds of the present invention will be applied directly to the foliage and other plant parts. Generally they are effective against weed grasses as well as broadleaved weeds. Some may be selective with respect to type of application and/or type of weed.

The amount of compound of this invention administered will vary with the particular plant part or plant growth medium which is to be contacted, the general location of application, i.e., sheltered areas such as greenhouses as compared to exposed areas such as fields, as well as the desired type of control. For pre-emergent control of most plants, dosages in the range of about 0.5 to 20 lbs per acre will be used. Such administration will give a concentration of about 2 to 80 ppm compound distributed throughout 0.1 acre-foot. For post-emergent application, such as foliar spray application, compositions containing about 0.5 to 8 lbs compound per 100 gallons spray will be used. Such application is equivalent to about 0.5 to 20 lbs compound per acre.

The herbicidal compositions of this invention comprise an herbicidal amount of one or more of the above-described compounds intimately admixed with a biologically inert carrier. The carrier may be a liquid diluent such as water or acetone, or a solid. The solid may be in the form of dust powder or granules. These compositions will also usually contain adjuvants such as a wetting or dispersing agent to facilitate their penetration into the plant growth medium or plant tissue and generally enhance their effectiveness. These compositions may also contain other pesticides, stabilizers, conditioners, fillers, and the like.

Pre- and post-emergent herbicidal tests on representative compounds of this invention were made using the following methods. As used herein the terminology "an herbicidal composition" is used to mean only an herbicidal composition and excludes compositions for other uses such as insecticidal, pesticidal or the like other uses.

Pre-emergent Test

An acetone solution of the test compounds was prepared by mixing 750 mg compound, 220 mg of a nonionic surfactant and 25 ml of acetone. This solution was added to approximately 125 ml of water containing 156 mg of surfactant.

Seeds of the test vegetation were planted in a pot of soil and the test compound solution was sprayed uniformly onto the soil surface at a dose of 100 mg per cm$^2$. The pot was watered and placed in a greenhouse. The pot was watered intermittently and was observed for seedling emergence, health of emerging seedlings, etc., for a 3-week period. At the end of this period, the herbicidal effectiveness of the compound was rated based on the physiological observations. A 0- to-100 scale was used, 0 representing no phytotoxicity, 100 representing complete kill.

Post-emergent Test

The test compound was formulated in the same manner as described above for the pre-emergent test. The concentration of the compound in the formulation was 5000 ppm. This formulation was uniformly sprayed on 2 duplicate pots of 24-day-old plants (approximately 15 to 25 plants per pot) at a dose of 100 mg per cm$^2$. After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0- to 100 scale was used, 0 representing no phytotoxicity, 100 representing complete kill.

The results of these tests appear in Table II.

Certain compounds of the present invention find use as insecticides. The terms "insecticide" and "insect" as used herein refer to their broad and commonly understood usage rather than to those creatures which in the strict biological sense are classified as insects. Thus, the term "insect" is used not only to include small invertebrate animals belonging to the Insecta, insecta, but also to other related classes of arthropods whose members are segmented invertebrates having more or fewer than six legs, such as spiders, mites, ticks, centipedes, worms, and the like.

The compounds of the present invention may be applied in either liquid or solid formulations to the insects, their environment or hosts susceptible to insect attack. For example, they may be sprayed or otherwise applied directly to plants or soil so as to effect control of insects coming into contact therewith.

Formulations of the compounds of this invention will comprise a toxic amount of one or more of the compounds and a biologically inert carrier. Usually they will also contain a wetting agent. Solids carriers such as clay, talc, sawdust and the like may be used in such formulations. Liquid diluents which may be used with the compounds include water and aromatic solvents. In addition, these formulations may contain other compatible pesticides, fillers, stabilizers, attractants, and the like.

The concentration of the active ingredient to be used with inert carriers, either solid or liquid carriers, will be dependent upon many factors, such as the particular compound which is used, the carrier in or upon which it is incorporated, the method and conditions of application, the insect species to be controlled, etc., the proper consideration of these factors being within the skill of those versed in the art. In general, the toxic ingredients of this invention will be effective in concentrations from about 0.0001% by weight to as high as 50% by weight or higher. Economically, of course, it is desirable to use lower concentrations of this active ingredient. Thus, it is usually desirable to use less than 20% by weight of the active ingredient in a particular composition.

The following tests were conducted with certain compounds of the present invention to show thier insecticidal activity. The test results are reported in Table III.

Test Procedures

Houseflies (*Musca Domestica L.*) —A 500-ppm acetone solution of the candidate toxicant was placed in a microsprayer (atomizer). A random mixture of anesthesized male and female flies was placed in a container and 55 mg of the above-described acetone solution was sprayed on it. A lid was placed on the container. A mortality reading was made after 24 hours.

Aphids (*Aphis gossypii* Glover) — An acetone solution of the candidate toxicant containing a small amount of nonionic emulsifier was diluted with water to a particular concentration. Cucumber leaves infested with the cotton aphids were dipped in the toxicant solution. mortality readings were than taken after 24 hours.

Certain compounds of the present invention also exhibit fungicidal activity. When used as fungicides, the compound will be formulated and applied in fungicidal amounts by conventional art methods to fungi or hosts which are subject to fungus attack, especially vegetative hosts such as plants, plant seeds, etc. The amount used will vary, of course, dependent upon several factors such as the host, the type of fungus, etc. The compound may be combined with inert liquids or solid carriers as powders, solutions, dispersions, etc. If so combined, the amount will generally be in an amount from 0.005 to 95% by weight, preferably 1 to 50% by weight. Suitable liquid carriers include water, kerosene, xylene, alcohols, alkylated naphthalene and glycols. Solid carriers include kaolin clays, diatomaceous earth, silica, talc, etc.

Fungicidal formulations may also contain stabilizers, spreading agents, sticking agents, fillers, other compatible pesticides, and the like.

TABLE I

| Ex. No. | Name | Analysis Calculated S | P | Hal.* | Found S | P | Hal.* |
|---|---|---|---|---|---|---|---|
| 7 | i-Butyl-S,S-ethylene phosphorodithioites | 32.7 | 15.8 | | 32.2 | 15.5 | |
| 8 | Methyl-S,S-ethylene phosphorodithioites | 41.6 | 20.1 | | 40.2 | 19.4 | |
| **9 | Ethyl-S,S-ethylene phosphorodithioites | 38.1 | 18.4 | | 38.2 | 18.3 | |
| 10 | Propyl-S,S-ethylene phosphorodithioites | 35.2 | 17.0 | | 34.7 | 16.3 | |
| 11 | Isopropyl-S,S-ethylene phosphorodithioites | 35.2 | 17.0 | | 35.0 | 16.8 | |
| 12 | n-Butyl-S,S-ethylene phosphorodithioites | 32.7 | 15.8 | | 31.0 | 15.5 | |
| 13 | s-Butyl-S,S-ethylene phosphorodithioites | 32.7 | 15.8 | | 32.9 | 15.7 | |
| 14 | Neopentyl-S,S-ethylene phosphorodithioites | 30.5 | 14.8 | | 29.0 | 14.0 | |
| 15 | 2-(3,3-dimethyl)butyl-S,S-ethylene phosphorodithioites | 28.6 | 13.8 | | 27.3 | 12.5 | |
| 16 | Allyl-S,S-ethylene phosphorodithioites | 35.6 | 17.2 | | 35.3 | 16.9 | |
| 17 | Cyclopentyl-S,S-ethylene phosphorodithioites | 30.8 | 14.9 | | 29.3 | 13.7 | |
| 18 | 2-Bromoethyl-S,S-ethylene phosphorodithioites | 26.0 | 32.3 | 32.3[1] | 26.0 | 12.2 | 33.3[1] |
| 19 | 1-Bromo-2-propyl-S,S-ethylene phosphorodithioites | 24.6 | 11.9 | 32.6[1] | 24.4 | 11.6 | 30.7[1] |
| 20 | 2-Ethoxyethyl-S,S-ethylene phosphorodithioites | 30.2 | 14.6 | | 30.2 | 14.6 | |
| 21 | 2-Methoxyethyl-S,S-ethylene phosphorodithioites | 32.3 | 15.6 | | 31.2 | 15.0 | |
| 22 | 3-Thiopentyl-S,S-ethylene phosphorodithioites | 42.1 | 13.6 | | 39.9 | 12.5 | |
| 23 | Methyl-S,S-1,2-propylene phosphorodithioites | 38.1 | 18.4 | | 37.5 | 18.2 | |
| 24 | Ethyl-S,S-1,2-propylene phosphorodithioites | 35.2 | 17.0 | | 34.1 | 17.1 | |
| 25 | Butyl-S,S-1,2-propylene phosphorodithioites | 30.5 | 14.7 | | 30.3 | 14.9 | |
| 26 | Isopentyl-S,S-1,2-propylene phosphorodithioites | 28.6 | 13.8 | | 28.3 | 13.5 | |
| 27 | n-Pentyl-S,S-1,2-propylene phosphorodithioites | 28.6 | 13.8 | | 28.7 | 13.4 | |
| 28 | Crotyl-S,S-1,2-propylene phosphorodithioites | 50.8 | 14.9 | | 30.7 | 14.8 | |
| 29 | Cyclopentyl-S,S-1,2-propylene phosphorodithioites | 28.9 | 13.9 | | 26.7 | 13.8 | |
| 30 | 1-Trichloromethylethyl-S,S-1,2-propylene phosphorodithioites | | 10.3 | 35.5[2] | | 9.8 | 33.8[2] |
| 31 | 2,2-Dichloroethyl-S,S-1,2-propylene phosphorodithioites | | 12.3 | 28.2[2] | | 11.9 | 27.7[2] |
| 32 | Benzyl-S,S-ethylene phosphorodithioites | 27.9 | 13.5 | | 28.4 | 12.8 | |
| 33 | 2-Phenylethyl-S,S-ethylene phosphorodithioites | 26.3 | 12.7 | | 26.3 | 12.3 | |
| 34 | 4-Methylbenzyl-S,S-ethylene phosphorodithioites | 26.3 | 12.7 | | 25.7 | 12.5 | |
| 35 | 1-Phenylpropyl-S,S-ethylene phosphorodithioites | 24.8 | 12.0 | | 24.3 | 11.2 | |
| 36 | 1-Phenylethyl-S,S-ethylene phosphorodithioites | 26.3 | 12.7 | | 26.5 | 12.3 | |
| 37 | Cinnamyl-S,S-ethylene phosphorodithioites | 25.1 | 12.1 | | 25.0 | 12.1 | |
| 38 | 4-Chlorobenzyl-S,S-ethylene phosphorodithioites | 24.2 | 11.7 | 13.4[2] | 23.3 | 11.5 | 13.5[2] |
| 39 | 3-Chlorobenzyl-S,S-ethylene phosphorodithioites | | 11.7 | 13.4[2] | | 11.8 | 13.0[2] |
| 40 | 4-Methylphenyl-S,S-ethylene phosphorodithioites | 27.9 | 13.5 | | 27.2 | 13.2 | |
| 41 | 4-s-Butylphenyl-S,S-ethylene phosphorodithioites | 23.6 | 11.4 | | 23.2 | 11.4 | |
| 42 | 2-s-Butylphenyl-S,S-ethylene phosphorodithioites | 23.6 | 11.4 | | 23.3 | 11.5 | |
| 43 | 3-s-Butylphenyl-S,S-ethylene phosphorodithioites | 23.6 | 11.4 | | 24.0 | 11.2 | |
| 44 | 2-t-Butylphenyl-S,S-ethylene phosphorodithioites | 23.6 | 11.4 | | 23.2 | 11.4 | |
| 45 | 3-t-Butylphenyl-S,S-ethylene phosphorodithioites | 23.6 | 11.4 | | 22.2 | 10.2 | |
| 46 | 2-Allylphenyl-S,S-ethylene phosphorodithioites | 25.1 | 12.1 | | 24.9 | 12.0 | |
| 47 | Pentachlorophenyl-S,S-ethylene phosphorodithioites | 16.5 | 8.0 | 45.6[2] | 15.8 | 7.6 | 44.5[2] |
| 48 | 2,5-Dichlorophenyl-S,S-ethylene phosphorodithioites | | 10.9 | 24.9[2] | | 10.3 | 24.5[2] |
| 49 | 2,3-Dichlorophenyl-S,S-ethylene phosphorodithioites | | 10.9 | 24.9[2] | | 10.3 | 24.7[2] |
| 50 | 2-Fluorophenyl-S,S-ethylene phosphorodithioites | 27.4 | 13.2 | | 27.0 | 12.8 | |
| 51 | 3,5-Dichlorophenyl-S,S-ethylene phosphorodithioites | 24.9 | 10.9 | | 22.8 | 10.7 | |
| 52 | 3-Methyl-4-chlorophenyl-S,S-ethylene phosphorodithioites | 24.2 | 11.7 | | 22.8 | 11.5 | |
| 53 | Benzyl-S,S-1,2-propylene phosphorodithioites | 26.3 | 12.7 | | 25.8 | 12.3 | |
| 54 | 2-Chloro-2-phenylethyl-S,S-1,2-propylene phosphorodithioites | | 10.6 | 12.1[2] | | 10.4 | 12.6[2] |
| 55 | 4-Methylphenyl-S,S-1,2-propylene phosphorodithioites | 26.3 | 12.7 | | 26.0 | 12.3 | |
| 56 | 4-s-Butylphenyl-S,S-1,2-propylene phosphorodithioites | 22.4 | 10.8 | | 22.3 | 10.9 | |
| 57 | 3-s-Butylphenyl-S,S-1,2-propylene phosphorodithioites | 22.4 | 10.8 | | 21.8 | 10.9 | |
| 58 | 4-Chlorophenyl-S,S-1,2-propylene phosphorodithioites | | 11.7 | 13.4[2] | | 11.7 | 12.7[2] |
| 59 | 3-Methyl-4-chlorophenyl-S,S-1,2-propylene phosphorodithioites | | 11.1 | 12.7[2] | | 9.8 | 10.8[2] |
| 60 | 2-Methyl-4-chlorophenyl-S,S-1,2-propylene phosphorodithioites | | 11.1 | 12.7[2] | | 9.8 | 11.1[2] |
| 61 | 2-Fluorophenyl-S,S-1,2-propylene phosphorodithioites | 25.8 | 12.5 | | 26.1 | 13.1 | |
| 62 | 4-Nitrophenyl-S,S-ethylene phosphorodithioites | 24.5 | 11.9 | | 24.3 | 11.8 | |
| 63 | 2-Methoxyphenyl-S,S-ethylene phosphorodithioites | 26.0 | 12.6 | | 25.8 | 12.5 | |
| 64 | 4-Methoxyphenyl-S,S-ethylene phosphorodithioites | 26.0 | 12.6 | | 26.0 | 12.2 | |
| 65 | 4-Nitrophenyl-S,S-trimethylene phosphorodithioites | | 11.3 | 5.1[3] | | 11.0 | 4.9[3] |
| 66 | 4-Nitrophenyl-S,S-1,2-propylene phosphorodithioites | 23.3 | | 5.1[3] | 22.5 | | 5.0[3] |
| 67 | 2,6-Dimethoxyphenyl-S,S-1,2-propylene phosphorodithioites | 22.1 | 10.7 | | 22.4 | 10.4 | |
| 68 | 2-Ethoxyethyl-S,S-1,2-propylene phosphorodithioites | 28.3 | 13.7 | | 28.3 | 13.5 | |
| 69 | 3-Thiopentyl-S,S-1,2-propylene phosphorodithioites | 39.7 | 12.8 | | 37.4 | 12.7 | |
| 70 | 2-Methoxyethyl-S,S-1,2-propylene phosphorodithioites | 30.2 | 14.6 | | 29.8 | 15.4 | |
| 71 | 1-Trichloromethylethyl-S,S-trimethylene phosphorodithioites | | 10.3 | 35.5[2] | | 10.1 | 34.9[2] |
| 72 | n-Butyl ethylene phosphorotrithioite | 45.2 | 14.6 | | 42.5 | 13.9 | |
| 73 | i-Butyl ethylene phosphorotrithioite | 45.2 | 14.6 | | 43.5 | 13.8 | |
| 74 | n-Pentyl ethylene phosphorotrithioite | 42.4 | 13.7 | | 41.9 | 13.6 | |
| 75 | i-Pentyl ethylene phosphorotrithioite | 42.5 | 13.7 | | 42.1 | 13.7 | |
| 76 | n-Hexyl ethylene phosphorotrithioite | 40.0 | 12.9 | | 39.9 | 12.7 | |

TABLE I-continued

| Ex. No. | Name | Analysis Calculated | | | Analysis Found | | |
|---|---|---|---|---|---|---|---|
| | | S | P | Hal.* | S | P | Hal.* |
| 77 | n-Decyl ethylene phosphorotrithioite | 32.4 | 10.5 | | 31.7 | 10.7 | |
| 78 | 2,2-Dichloroethylene phosphorotrithioite | 28.0 | 12.2 | | 27.0 | 12.6 | |
| 79 | Cyclohexyl ethylene phosphorotrithioite | 40.3 | 13.0 | | 40.2 | 12.7 | |
| 80 | Ethyl trimethylene phosphorotrithioite | 48.5 | 15.6 | | 44.4 | 16.3 | |
| 81 | n-Butyl trimethylene phosphorotrithioite | 42.5 | 13.7 | | 41.0 | 12.9 | |
| 82 | s-Butyl trimethylene phosphorotrithioite | 42.5 | 13.7 | | 40.1 | 13.7 | |
| 83 | 2,2-Dichloroethyl trimethylene phosphorotrithioite | 26.5 | 11.6 | | 25.7 | 11.0 | |
| 84 | i-Propyl-1,2-propylene phosphorotrithioite | 45.3 | 14.6 | | 43.4 | 14.3 | |
| 85 | n-Butyl-1,2-propylene phosphorotrithioite | 42.5 | 13.7 | | 42.5 | 13.4 | |
| 86 | n-Octyl-1,2-propylene phosphorotrithioite | 34.1 | 11.0 | | 33.3 | 10.8 | |
| 87 | n-Decyl-1,2-propylene phosphorotrithioite | 31.0 | 10.0 | | 29.3 | 10.1 | |
| 88 | Allyl-1,2-propylene phosphorotrithioite | 45.7 | 14.7 | | 43.9 | 14.3 | |
| 89 | 2,2-Dichloroethyl-1,2-propylene phosphorotrithioite | 26.5 | 11.6 | | 25.3 | 11.3 | |
| 90 | Benzyl ethylene phosphorotrithioite | 39.1 | 12.6 | | 38.6 | 11.9 | |
| 91 | 3-Phenylpropyl ethylene phosphorotrithioite | 35.1 | 11.3 | | 33.1 | 11.0 | |
| 92 | 4-Chlorobenzyl ethylene phosphorotrithioite | | 11.1 | 12.6[2] | | 11.1 | 12.4[2] |
| 93 | Phenyl ethylene phosphorotrithioite | 41.3 | 13.3 | | 38.7 | 12.4 | |
| 94 | 2-Methylphenyl ethylene phosphorotrithioite | 39.1 | 12.6 | | 37.6 | 12.0 | |
| 95 | 4-Chlorophenyl ethylene phosphorotrithioite | 36.0 | 11.6 | 13.3[2] | 35.8 | 11.6 | 13.6[2] |
| 96 | 4-Methylphenyl ethylene phosphorotrithioite | 39.1 | 12.6 | | 37.6 | 12.0 | |
| 97 | 4-t-Butylphenyl ethylene phosphorotrithioite | 33.4 | 10.7 | | 31.0 | 9.9 | |
| 98 | Benzyl ethylene phosphorotrithioite | 36.9 | 11.9 | | 33.4 | 12.0 | |
| 99 | Phenyl trimethylene phosphorotrithioite | 39.1 | 12.6 | | 37.2 | 12.1 | |
| 100 | 4-Chlorophenyl trimethylene phosphorotrithioite | 34.3 | 11.0 | | 31.9 | 11.2 | |
| 101 | 4-Nitrophenyl trimethylene phosphorotrithioite | 10.6 | | 4.8[3] | 10.0 | | 4.4[3] |
| 102 | Benzyl-1,2-propylene phosphorotrithioite | 36.9 | 11.9 | | 36.1 | 11.5 | |
| 103 | Phenyl-1,2-propylene phosphorotrithioite | 39.1 | 12.6 | | 38.0 | 11.4 | |
| 104 | 4-Chlorophenyl-1,2-propylene phosphorotrithioite | 12.6 | 11.0 | | 11.8 | 10.9 | |
| 105 | p-Chlorophenyl-S,S-ethylene phosphorodithioite | | | | | | |
| 106 | o-chlorophenyl-S,S-ethylene phosphorodithioite | | | | | | |
| 107 | O-2,4-dichlorophenyl ethylene phosphorodithioite | | | | | | |
| 108 | Phenyl-S,S-ethylene phosphorodithioite | | | | | | |
| 109 | O-methyl-1,2-propylene phosphorodithioite | | | | | | |
| 110 | 2,2-dichloroethyl-1,2-propylene phosphorotrithioite | | | | | | |
| 111 | O-2,2-dichloroethyl-1,2-propylene phosphorodithioite | | | | | | |
| 112 | Alkyl-1,2-propylene phosphorotrithioite | | | | | | |
| 113 | Isopropyl-1,2-propylene phosphorotrithioite | | | | | | |
| 114 | O-(2-chloro-2-phenyl)ethyl-1,2-propylene phosphorodithioite | | | | | | |
| 115 | O-1-trichloromethylethyl-1,2-propylene phosphorodithioite | | | | | | |
| 116 | O-2-bromoethyl-1,2-propylene phosphorodithioite | | | | | | |

*Halogens:
[1]Br;
[2]Cl;
[3]Nitrogen Analysis
**Prior art composition

| 117 | Phenyl-1,3-propylene phosphorotrithioite |
| 118 | Benzyl-1,3-propylene phosphorotrithioite |
| 119 | n-Butyl-1,3-propylene phosphorotrithioite |
| 120 | Sec-butyl-1,3-propylene phosphorotrithioite |
| 121 | 2,2-Dichloroethyl-1,3-propylene phosphorotrithioite |
| 122 | Ethyl-1,3-propylene phosphorotrithioite |
| 123 | 1-Trichloromethylethyl-S,S-1,3-propylene phosphorodithioite |
| 124 | O-p-nitrophenyl-3-propylene phosphorodithioite |
| 125 | 2-Fluorophenyl-1,3-propylene phosphorodithioite |
| 126 | Carbethoxy methyl-1,3-propylene phosphorotrithioite |

TABLE II

HERBICIDAL ACTIVITY -- % CONTROL (PRE/POST)

| Ex. No. | O | C | W | M | P | L | Ex. No. | O | C | W | M | P | L |
|---|---|---|---|---|---|---|---|---|---|---|---|---|---|
| 4 | 0/10 | 0/10 | 0/10 | —/90 | 0/96 | 0/96 | 64 | 0/78 | 0/— | 0/100 | 0/100 | 0/100 | 0/100 |
| 6 | 0/22 | 0/39 | 0/40 | 0/100 | 0/100 | 0/100 | 65 | 75/20 | 55/85 | 60/100 | 0/100 | 30/80 | 0/100 |
| 18 | 0/0 | 0/0 | 0/0 | —/99 | 0/90 | 0/90 | 66 | 0/22 | 0/60 | 0/60 | 0/96 | 0/78 | 0/39 |
| 23 | 0/22 | 0/3 | 0/3 | 0/100 | 0/100 | 0/— | 67 | —/78 | —/60 | —/90 | 0/100 | 0/96 | 0/100 |
| 27 | —/60 | —/39 | —/60 | 32/100 | 4/96 | 10/100 | 69 | 0/3 | 0/10 | 0/39 | 0/100 | 0/100 | 0/100 |
| 30 | 39/60 | 78/96 | 10/96 | 60/39 | 90/78 | 39/78 | 71 | —/10 | —/10 | —/39 | 0/100 | 0/100 | 0/100 |
| 31 | 0/0 | 0/22 | 0/22 | 0/96 | 0/96 | 0/96 | 74 | 0/90 | 0/39 | 0/39 | 0/100 | 0/90 | 0/99 |
| 32 | 0/0 | 0/0 | 0/0 | —/100 | 0/100 | 0/100 | 76 | 10/100 | 22/99 | 10/100 | 0/100 | 0/100 | 0/100 |
| 34 | 0/22 | 0/39 | 0/39 | 0/100 | 0/100 | 0/100 | 77 | 0/22 | 0/0 | 0/0 | 0/100 | 0/100 | 0/100 |
| 37 | 0/0 | 0/4 | 0/39 | 0/96 | 0/90 | 0/96 | 78 | 0/39 | 0/39 | 0/39 | 0/100 | 0/100 | 0/100 |
| 38 | 0/10 | 22/0 | 0/0 | 0/100 | 0/100 | 0/100 | 79 | 0/0 | 0/90 | 0/10 | 0/100 | 0/100 | 0/100 |
| 39 | 0/39 | 0/39 | 0/60 | 0/100 | 0/100 | 0/100 | 80 | 10/0 | 0/0 | 22/0 | 0/100 | 0/100 | 0/100 |
| 40 | 0/90 | 0/60 | 0/90 | 0/100 | 0/100 | 0/100 | 81 | 0/3 | 0/— | 0/22 | 0/100 | 0/100 | 0/100 |
| 42 | 0/22 | 0/60 | 0/60 | 0/100 | 0/100 | 0/100 | 82 | 0/39 | 22/60 | 22/59 | 0/100 | 22/100 | 22/100 |
| 43 | 10/39 | 0/22 | 0/60 | 0/100 | 0/100 | 0/100 | 83 | —/39 | —/39 | —/39 | 0/100 | 22/100 | 0/100 |
| 45 | 0/3 | 0/39 | 0/22 | 0/100 | 0/100 | 0/100 | 84 | 3/22 | 0/39 | 0/39 | 0/100 | 0/100 | 0/100 |
| 47 | 10/78 | 22/78 | 96/60 | 99/100 | 22/100 | 22/100 | 85 | 0/10 | 0/— | 0/39 | 0/100 | 0/100 | 10/100 |
| 48 | 22/10 | 0/— | 0/39 | 0/100 | 0/100 | 0/100 | 86 | —/60 | —/39 | —/96 | 0/100 | 22/100 | 10/100 |
| 49 | 0/22 | 0/22 | 0/39 | 0/100 | 0/100 | 0/100 | 87 | 0/100 | 0/98 | 99/100 | 0/100 | 0/100 | 0/100 |
| 50 | 0/60 | 0/78 | 0/96 | 0/100 | 0/100 | 0/100 | 88 | 0/10 | 0/10 | 0/10 | 4/100 | 0/100 | 0/100 |
| 51 | 0/78 | 0/60 | 0/60 | 0/100 | 0/100 | 0/— | 89 | 0/5 | 25/40 | 25/90 | 25/100 | 15/100 | 0/100 |
| 52 | 0/96 | 0/96 | 0/96 | 0/100 | 0/100 | 0/100 | 90 | 0/22 | 0/3 | 0/3 | 0/99 | 0/99 | 0/99 |
| 53 | —/22 | —/22 | —/60 | —/100 | —/100 | —/100 | 91 | 0/22 | 0/39 | 10/39 | 10/100 | 0/100 | 0/100 |

TABLE II-continued

HERBICIDAL ACTIVITY -- % CONTROL (PRE/POST)

| Ex. No. | O | C | W | M | P | L | Ex. No. | O | C | W | M | P | L |
|---|---|---|---|---|---|---|---|---|---|---|---|---|---|
| 54 | 0/3 | 0/3 | 0/3 | 0/100 | 0/100 | 0/— | 92 | 0/78 | 0/78 | 0/90 | 0/100 | 0/100 | 0/100 |
| 55 | 0/90 | 0/90 | 0/22 | 0/100 | 0/100 | 0/100 | 93 | 0/10 | 0/10 | —/— | —/90 | 0/96 | 0/96 |
| 56 | 0/100 | 0/100 | 0/100 | 0/100 | 0/100 | 0/100 | 96 | 0/96 | 0/99 | 0/96 | 0/100 | 0/100 | 0/100 |
| 57 | 0/96 | 0/96 | 10/100 | 0/100 | 0/100 | 0/100 | 97 | 0/22 | 0/80 | 0/22 | 0/100 | 0/100 | 0/100 |
| 58 | 0/0 | 0/10 | 0/22 | 10/100 | 10/100 | 10/100 | 98 | 0/0 | 0/0 | 0/39 | 0/90 | 0/90 | 0/100 |
| 59 | 20/15 | 40/40 | 50/80 | 15/95 | 15/95 | 0/95 | 99 | 10/0 | 10/22 | 10/22 | 0/100 | 0/100 | 0/100 |
| 60 | 0/0 | 10/20 | 25/75 | 0/85 | 0/85 | 0/100 | 102 | 0/10 | 0/39 | 0/100 | 0/100 | 0/100 | 0/100 |
| 61 | 0/96 | 0/96 | 0/96 | 0/100 | 0/99 | 0/100 | 103 | 0/10 | 0/60 | 0/100 | 0/100 | 0/100 | 0/100 |
| 62 | 0/10 | 0/22 | 0/10 | —/100 | 0/100 | 0/100 | 104 | —/22 | —/39 | —/22 | —/100 | —/100 | —/100 |
| 63 | 10/78 | 10/— | 10/78 | 22/100 | 10/90 | 22/96 | | | | | | | |

O = Wild Oats (*Avena fatua*)
W = Watergrass (*Echinochloa crusgalli*)
C = Crabgrass (*Digitaria sanguinalis*)
M = Mustard (*Brassica arvensis*)
P = Pigweed (*Amaranthus retroflexus*)
L = Lambsquarter (*Chenopodium album*)

TABLE IIA

Herbicidal Activity (Including Many Structurally Close Inactive Compounds) - % Control (Pre/Post)

| Ex. No. | O | C | W | M | P | L |
|---|---|---|---|---|---|---|
| 1 | 0/0 | 0/0 | 0/0 | 0/0 | 0/0 | 0/0 |
| 2 | 3/9 | 22/0 | 0/0 | —/39 | 10/39 | 0/39 |
| 3 | 0/0 | 0/0 | 0/0 | 0/0 | 0/0 | 0/0 |
| 5 | 10/39 | 90/96 | 0/78 | 9/100 | 0/99 | 0/100 |
| 7 | 0/4 | 0/22 | 0/— | 0/39 | 0/78 | 0/78 |
| 8 | 0/0 | 0/0 | 0/0 | 0/0 | 0/0 | 0/0 |
| 9 | 0/0 | 0/0 | 0/0 | 0/0 | 0/0 | 0/0 |
| 10 | 0/22 | 0/60 | 0/22 | 0/10 | 0/10 | 0/10 |
| 11 | 0/0 | 0/0 | 0/0 | 0/0 | 0/0 | 0/0 |
| 12 | 0/0 | 0/0 | 0/0 | 0/0 | 0/0 | 0/0 |
| 13 | 0/0 | 0/0 | 0/0 | 0/0 | 0/10 | 0/0 |
| 15 | 0/0 | 0/22 | 0/0 | 0/10 | 0/10 | 0/10 |
| 16 | 0/0 | 0/100 | 0/0 | 0/99 | 0/22 | 0/22 |
| 17 | 0/10 | 0/0 | 0/0 | 0/0 | 0/0 | 0/0 |
| 19 | 0/0 | 0/0 | 0/0 | 0/0 | 0/0 | 0/0 |
| 20 | 0/0 | 0/0 | 0/0 | 0/0 | 0/0 | 0/0 |
| 21 | 0/0 | 0/0 | 0/0 | 0/78 | 0/22 | 0/78 |
| 22 | 0/0 | 0/0 | 0/0 | 0/0 | 0/0 | 0/0 |
| 25 | 0/0 | 0/0 | 0/— | 0/10 | 0/10 | 0/10 |
| 26 | 0/0 | 0/0 | 0/0 | 0/0 | 0/0 | 0/0 |
| 28 | 0/0 | 0/0 | 0/0 | 0/0 | 0/0 | 0/0 |
| 29 | 0/0 | 22/0 | 10/0 | 0/0 | 0/0 | 0/0 |
| 33 | 0/22 | 0/39 | 0/60 | 0/90 | 0/22 | 0/60 |
| 35 | 0/10 | 60/10 | 0/39 | 0/22 | 0/22 | 0/39 |
| 36 | 0/10 | 0/0 | 0/10 | 0/22 | 0/22 | 0/39 |
| 41 | 0/0 | 0/0 | 0/0 | 0/0 | 0/0 | 0/0 |
| 46 | 0/0 | 0/22 | 0/0 | 0/22 | 0/0 | 0/0 |
| 68 | 0/78 | 0/90 | 0/90 | 0/100 | 0/100 | 0/100 |
| 70 | 0/0 | 0/0 | 0/0 | 0/0 | 0/10 | 0/10 |
| 72 | 0/3 | 0/39 | 0/10 | 0/100 | 0/100 | 0/100 |
| 73 | 0/0 | 0/0 | 0/0 | 0/0 | 0/0 | 0/0 |
| 75 | 0/0 | 0/0 | 0/0 | 0/0 | 0/0 | 0/0 |
| 94 | 0/22 | 10/39 | 0/39 | 10/100 | 0/100 | 0/100 |
| 95 | 0/78 | 0/90 | 0/78 | 0/100 | 0/100 | 0/100 |
| 100 | 0/22 | 0/22 | 0/80 | 0/100 | 0/100 | 0/100 |
| 101 | 0/0 | 0/39 | 0/0 | 0/90 | 0/90 | 0/100 |
| 105 | 0/0 | 0/0 | — | 0/0 | 0/0 | 0/0 |
| 106 | 0/10 | 0/0 | 0/0 | 0/39 | 0/39 | 0/22 |
| 107 | 0/4 | 0/39 | 22/4 | 0/0 | 0/0 | 0/0 |
| 108 | 0/22 | 0/22 | 0/22 | 0/90 | 0/90 | 0/90 |
| 109 | 0/22 | 0/3 | 0/3 | 0/100 | 0/100 | 0/ |
| 110 | 0/5 | 25/90 | 25/40 | 25/100 | 15/100 | 0/100 |
| 111 | 0/0 | 0/22 | 0/22 | 0/96 | 0/96 | 0/96 |
| 112 | 0/10 | 0/10 | 0/10 | 4/100 | 0/100 | 0/100 |
| 113 | 3/22 | 0/39 | 0/100 | 0/100 | 0/100 | 0/100 |
| 114 | 0/3 | 0/3 | 0/3 | 0/100 | 0/100 | 0/ |
| 115 | 39/60 | 10/96 | 78/96 | 60/39 | 90/78 | 39/78 |
| 116 | 0/0 | 0/0 | 0/10 | 0/60 | 0/78 | 0/78 |
| 117 | 0/0 | 10/22 | 10/22 | 0/100 | 0/100 | 0/100 |
| 118 | 0/0 | 0/39 | 0/0 | 0/90 | 0/90 | 0/100 |
| 119 | 0/3 | 0/22 | 0/2 | 0/100 | 0/100 | 0/100 |
| 120 | 0/39 | 22/39 | 22/60 | 0/100 | 0/100 | 0/100 |
| 121 | —/39 | —/39 | —/39 | 0/100 | 22/100 | 22/100 |
| 122 | 10/0 | 22/0 | 0/0 | 0/100 | 0/100 | 0/100 |
| 123 | —/10 | —/39 | —/0 | 0/100 | 0/100 | 0/100 |
| 124 | 75/20 | 60/100 | 55/85 | 0/100 | 50/80 | 0/100 |
| 125 | 0/22 | 0/90 | 0/39 | 0/100 | 0/100 | 0/100 |
| 126 | 10/39 | 90/96 | 0/78 | 0/100 | 0/99 | 0/100 |

TABLE III

INSECTICIDAL ACTIVITY % CONTROL (CONC. IN PPM)

| Ex. No. | Aphids | Flies |
|---|---|---|
| 1 | 100 (15.6) | — |
| 2 | 100 (30) | 100 (500) |
| 3 | 96 (30) | — |
| 7 | 100 (10) | — |
| 8 | — | 100 (500) |
| 9 | 10 (30) | 100 (500) |
| 10 | — | 98 (500) |
| 11 | 96 (30) | 98 (500) |
| 12 | 99 (30) | 90 (500) |
| 13 | 96 (30) | — |
| 14 | 96 (30) | — |
| 15 | 100 (25) | — |
| 17 | 100 (16) | 60 (500) |
| 19 | 94 (30) | — |
| 20 | 90 (30) | 90 (500) |
| 21 | 99 (30) | 90 (500) |
| 22 | 100 (30) | — |
| 25 | 99 (30) | — |
| 27 | 100 (16) | — |
| 28 | 58 (30) | — |
| 29 | 98 (10) | — |
| 31 | 98 (10) | — |
| 32 | 98 (15.6) | — |
| 33 | 100 (30) | — |
| 34 | 100 (10) | — |
| 35 | 100 (30) | — |
| 36 | 100 (25) | — |
| 37 | 99 (30) | — |
| 39 | 100 (25) | — |
| 41 | 100 (30) | — |
| 46 | 99 (30) | — |
| 48 | — | 100 (500) |
| 68 | 100 (25) | 39 (500) |
| 69 | 100 (10) | — |
| 70 | 84 (30) | — |
| 72 | 100 (15.6) | 30 (500) |
| 73 | 100 (6.4) | 100 (500) |
| 75 | 100 (2.5) | 50 (500) |
| 79 | 100 (10) | — |

What is claimed is:

1. A method of controlling the growth of undesirable vegetation comprising applying to the undesired vegetation or the growth medium of the vegetation, an herbicidally effective amount of a compound of the formula

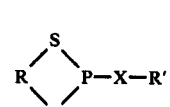

wherein
(a) when R is phenyl; dimethylene, X is oxygen and R' is phenyl substituted with 1 to 5 halogen atoms; phenyl substituted with one alkyl group of 1 to 2 carbon atoms; phenyl substituted with one nitro group; benzyl; or benzyl substituted with a chlorine or a methyl group; or
(b) when R is dimethylene and X is sulfur, R' is phenyl; cycloalkyl of 5 to 6 carbon atoms in the ring; or normal alkyl of 5 to 10 carbon atoms; or
(c) when R is 1,2-propylene or trimethylene and X is oxygen or sulfur, R' is normal alkyl of 1 to 10 carbon atoms; normal alkyl of 1 to 10 carbon atoms substituted with 1 to 3 halogen atoms; phenyl; phenyl substituted with 1 to 5 halogen atoms, an alkyl group of 1 to 4 carbon atoms or a nitro group; benzyl; benzyl substituted with 1 to 5 halogen atoms, an alkyl group of 1 to 4 carbon atoms or a nitro group; or alkylene radical of 1 to 3 carbon atoms substituted with a carbalkoxy group of 2 to 6 carbon atoms.

2. A method in accordance with claim 1 wherein
(a) when R is dimethylene and X is oxygen, R' is phenyl or phenyl substituted with 2 to 5 fluorine or chlorine atoms or phenyl substituted with one fluorine atom; phenyl substituted with one alkyl group of 1 to 2 carbon atoms; phenyl substituted with one nitro group; benzyl; or benzyl substituted with a chlorine or methyl group; or
(b) when R is dimethylene and X is sulfur, R' is phenyl; cycloalkyl of 5 to 6 carbon atoms; or normal alkyl of 5 to 10 carbon atoms; or
(c) when R is 1,2-propylene or trimethylene and X is oxygen or sulfur, R' is normal alkyl of one carbon atom or 3 to 10 carbon atoms either unsubstituted or substituted with 1 to 3 halogen atoms; phenyl; phenyl substituted with 1 to 5 halogen atoms; an alkyl group of 1 to 4 carbon atoms or a nitro group; benzyl; benzyl substituted with 1 to 5 halogen atoms, an alkyl group of 1 to 4 carbon atoms or a nitro group.

3. A method of controlling the growth of undesirable broad-leaf vegetation comprising applying to the undesirable broad-leaf vegetation or the growth medium of the vegetation after such vegetation has emerged from the growth medium an herbicidally effective amount of a compound of the formula

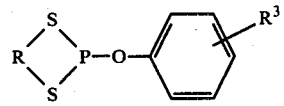

wherein R is ethylene or 1,2-propylene and $R^3$ is a $C_1$-$C_2$ alkyl,

4. A method of controlling the growth of undesirable broad-leaf vegetation comprising applying to the undesirable broad-leaf vegetation or the growth medium of the vegetation after such vegetation has emerged from the growth medium an herbicidally effective amount of a compound of the formula

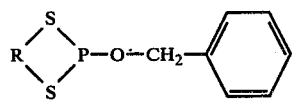

wherein R is ethylene or 1,2-propylene.

5. A method of controlling the growth of undesirable vegetation comprising applying to the undesirable vegetation or the growth medium of the vegetation after the vegetation has emerged from the growth medium an herbicidally effective amount of carbethoxy methyl-1,3-propylene phosphorotrithioite.

* * * * *

UNITED STATES PATENT AND TRADEMARK OFFICE
CERTIFICATE OF CORRECTION

PATENT NO. : 4,140,514
DATED : February 20, 1979
INVENTOR(S) : Francis J. Freenor, III It is certified that error appears in the above-identified patent and that said Letters Patent are hereby corrected as shown below:

In the title of invention, "DITHIOPHOSPITES" should read --DITHIOPHOSPHITES--.

Col. 1, line 25, "(1970). No." should read --(1970).--.

Col. 3, lines 60-61, "ethyltiomethyl" should read --ethylthiomethyl--.

Col. 4, line 47, "thiphenol" should read --thiophenol--.

Col. 5, line 37, "PCL$_3$" should read --PCl$_3$--.

Col. 6, line 44, "0.322 mol" should read --0.0322 mol--.

Col. 8, line 24, "Insecta, insecta" should read --class Insecta--.

Signed and Sealed this

Sixteenth Day of October 1979

[SEAL]

Attest:

RUTH C. MASON
*Attesting Officer*

LUTRELLE F. PARKER
*Acting Commissioner of Patents and Trademarks*